(12) United States Patent
Gnjatic et al.

(10) Patent No.: US 7,009,035 B2
(45) Date of Patent: Mar. 7, 2006

(54) ISOLATED PEPTIDES WHICH BIND TO HLA-C MOLECULES AND USES THEREOF

(75) Inventors: Sacha Gnjatic, New York, NY (US); Lloyd J. Old, New York, NY (US); Yasuhiro Nagata, New York, NY (US); Elke Jager, Frankfurt am Main (DE); Yao-Tseng Chen, New York, NY (US); Alexander Knuth, Frankfurt am Main (DE)

(73) Assignees: Ludwig Institute for Cancer Research, New York, NY (US); Cornell Research Foundation, Inc., Ithaca, NY (US); Memorial Sloan-Kettering Cancer Center, New York, NY (US)

( * ) Notice: Subject to any disclaimer, the term of this patent is extended or adjusted under 35 U.S.C. 154(b) by 438 days.

(21) Appl. No.: 10/274,017

(22) Filed: Oct. 18, 2002

(65) Prior Publication Data

US 2003/0050451 A1 Mar. 13, 2003

Related U.S. Application Data

(62) Division of application No. 09/670,456, filed on Sep. 26, 2000, now Pat. No. 6,506,875.

(51) Int. Cl.
 *C07K 7/00* (2006.01)

(52) U.S. Cl. .................................... 530/328

(58) Field of Classification Search ............ 530/328
 See application file for complete search history.

(56) References Cited

PUBLICATIONS

Gnjatic, et al., "Strategy for monitoring T Cell Responses to NY–ESO–I In Patents With Any HLA Allele," Proc. Natl. Acad. Sci. 97(20): 10917–10922 (Sep. 26, 2000, Not Prior Art).

Jäger, et al., "Induction of primary NY–ESO–I Immunity: CD8+ T lymphocyte and antibody responses in peptide vaccinated patients with NY–ESO–I+ Cancers," Proc. Natl. Acad. Sci. 97 (22d: 12198–12203 (Oct. 24, 2000).

*Primary Examiner*—Christina Chan
*Assistant Examiner*—F. Pierre VanderVegt
(74) *Attorney, Agent, or Firm*—Fulbright & Jaworski L.L.P.

(57) ABSTRACT

The invention teaches peptide epitopes which bind to HLA-Cw3 and HLA-Cw6 molecules on the surface of cells. The peptides are useful diagnostically and therapeutically, as are DNA molecules which encode them, and the cytolytic T lymphocytes specific to the HLA/peptide complexes. Also a feature of the invention is a method for identifying relevant molecules such as those described herein, in a system that uses stimulation and restimulation using different viral vectors.

5 Claims, No Drawings

ISOLATED PEPTIDES WHICH BIND TO HLA-C MOLECULES AND USES THEREOF

RELATED APPLICATIONS

This application is a divisional application of Ser. No. 09/670,456 filed Sep. 26, 2000 now U.S. Pat. No. 6,506,875.

FIELD OF THE INVENTION

This invention relates to peptides which are useful in the context of cellular immunology. More particularly, the invention relates to peptides which bind to HLA molecules on the surface of cells. At least some of these peptides also induce the activation of cytolytic T cells, when they are complexed with their partner HLA molecule. Also a part of the invention are the uses of these peptides in areas such as identifying HLA-Cw3 and HLA-Cw6 positive cells, provoking T cells, determining presence of particular T cells, as well as cytolytic T cells themselves.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., *J. Natl. Canc. Inst.* 18:769–778 (1957); Klein et al., *Cancer Res.* 20:1561–1572 (1960); Gross, *Cancer Res.* 3:326–333 (1943), Basombrio, *Cancer Res.* 30:2458–2462 (1970) for general teachings on inducing tumors with chemical carcinogens and differences in cell surface antigens. This class of antigens has come to be known as "tumor specific transplantation antigens" or "TSTAs." Following the observation of the presentation of such antigens when induced by chemical carcinogens, similar results were obtained when tumors were induced in vitro via ultraviolet radiation. See Kripke, *J. Natl. Canc. Inst.* 53:333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., *Brit. J. Cancer* 33:241–259 (1976). The family of tum antigen presenting cell lines are immunogenic variants obtained by mutagenesis of mouse tumor cells or cell lines, as described by Boon et al., *J. Exp. Med.* 152:1184–1193 (1980), the disclosure of which is incorporated by reference. To elaborate, tum antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., *Proc. Natl. Acad. Sci. USA* 74:272 (1977), the disclosure of which is incorporated by reference. Many tumor types have been shown to exhibit this phenomenon. See, e.g., Frost et al., *Cancer Res.* 43:125 (1983). It appears that tum⁻ variants fail to form progressive tumors because they initiate an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., *Proc. Natl. Acad. Sci. USA* 76:5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., *J. Exp. Med.* 152:1175–1183 (1980)). Further evidence includes the observation that mice acquire an immune memory which permits them to resist subsequent challenge to the same turn variant, even when immunosuppressive amounts of radiation are administered with the following challenge of cells (Boon et al., *Proc. Natl. Acad. Sci. USA* 74:272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., *J. Exp. Med.* 157:1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., *Cancer Res.* 48:2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro, i.e., the study of the identification of the antigen by a particular cytolytic T cell ("CTL" hereafter) subset. The subset proliferates upon recognition of the presented tumor rejection antigen, and the cells presenting the tumor rejection antigens are lysed. Characterization studies have identified CTL clones which specifically lyse cells expressing the tumor rejection antigens. Examples of this work may be found in Levy et al., *Adv. Cancer Res.* 24:1–59 (1977); Boon et al., *J. Exp. Med.* 152:1184–1193 (1980); Brunner et al., *J. Immunol.* 124:1627–1634 (1980); Maryanski et al., *Eur. J. Immunol.* 124:1627–1634 (1980); Maryanski et al., *Eur. J. Immunol.* 12:406–412 (1982); Palladino et al., *Cancer. Res.* 47:5074–5079 (1987). This type of analysis is required for other types of antigens recognized by CTLs, including minor histocompatibility antigens, the male specific H-Y antigens, and the class of antigens referred to as "tum⁻" antigens, and discussed herein.

A tumor exemplary of the subject matter described supra is known as P815. See DePlaen et al., *Proc. Natl. Acad. Sci. USA* 85:2274–2278 (1988); Szikora et al., *EMBO J.* 9:1041–1050 (1990), and Sibille et al., *J. Exp. Med.* 172:35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum variants following mutagenesis, including variants referred to as P91A (DePlaen, supra), 35B (Szikora, supra), and P198 (Sibille, supra). In contrast to tumor rejection antigens—and this is a key distinction—the tum antigens are only present after the tumor cells are mutagenized. Tumor rejection antigens are present on cells of a given tumor without mutagenesis. Hence, with reference to the literature, a cell line can be tum+, such as the line referred to as "P11," and can be provoked to produce turn variants. Since the tum− phenotype differs from that of the parent cell line, one expects a difference in the DNA of tum cell lines as compared to their tum+ parental lines, and this difference can be exploited to locate the gene of interest in tune cells. As a result, it was found that genes of tum variants such as P91A, 35B and P198 differ from their normal alleles by point mutations in the coding regions of the gene. See Szikora and Sibille, supra, and Lurquin et al., *Cell* 58:293–303 (1989). This has proved not to be the case with the TRAs of this invention. These papers also demonstrated that peptides derived from the tum− antigen are presented by H-$2^d$ Class I molecules for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., *Science* 254:1643 (1991). It is now clear that the various genes of the MAGE family are expressed in tumor cells, and can serve as markers for the diagnosis of such tumors, as well as for other purposes discussed therein. See also Traversari et al., *Immunogenetics* 35:145 (1992); van der Bruggen et al., *Science* 254:1643 (1991) and DePlaen, et al., *Immunogenetics* 40:360 (1994). The mechanism by which a protein is processed and presented on a cell surface has now been fairly well documented. A cursory review of the development of the field may be found in Barinaga, "Getting Some 'Backbone':How MHC Binds Peptides," *Science* 257:880 (1992); also, see Fremont et al., *Science* 257:919 (1992); Matsumura et al., *Science* 257:927 (1992); Engelhard, *Ann. Rev. Immunol.* 12:181–207 (1994); Madden, et al., *Cell* 75:693–708 (1993); Ramensee, et al., *Ann. Rev. Immunol.* 11:213–244(1993); Germain, *Cell* 76:287–299(1994). These papers generally point to a requirement that the peptide which binds to an MHC/HLA molecule be nine amino acids long (a "nonapeptide"), and to the importance of the second and ninth residues of the nonapeptide. For H-$2k^b$, the anchor residues are positions 5 and 8 of an octamer, for H-$2D^b$, they are positions 5 and 9 of a nonapeptide while the anchor residues for HLA-A1 are positions 3 and 9 of a nonamer. Generally, for HLA molecules, positions 2 and 9 are anchors.

Studies on the MAGE family of genes have now revealed that a particular nonapeptide is in fact presented on the surface of some tumor cells, and that the presentation of the nonapeptide requires that the presenting molecule be HLA-A1. Complexes of the MAGE-1 tumor rejection antigen (the "TRA" or "nonapeptide") leads to lysis of the cell presenting it by cytolytic T cells ("CTLs").

Research presented in, e.g., U.S. Pat. No. 5,405,940 filed Aug. 31, 1992, and in U.S. Pat. No. 5,571,711, found that when comparing homologous regions of various MAGE genes to the region of the MAGE-1 gene coding for the relevant nonapeptide, there is a great deal of homology. Indeed, these observations lead to one of the aspects of the invention disclosed and claimed therein, which is a family of nonapeptides all of which have the same N-terminal and C-terminal amino acids. These nonapeptides were described as being useful for various purposes which includes their use as immunogens, either alone or coupled to carrier peptides. Nonapeptides are of sufficient size to constitute an antigenic epitope, and the antibodies generated thereto were described as being useful for identifying the nonapeptide, either as it exists alone, or as part of a larger polypeptide.

The preceding survey of the relevant literature shows that various peptides, usually eight, nine, or ten amino acids in length, complex with MHC molecules and present targets for recognition by cytolytic T cells. A great deal of study has been carried out on melanoma, and melanoma antigens which are recognized by cytolytic T cells are now divided into three broad categories. The first, which includes many of the antigens discussed, supra, (e.g., MAGE), are expressed in some melanomas, as well as other tumor types, and normal testis and placenta. The antigens are the expression product of normal genes which are usually silent in normal tissues.

A second family of melanoma antigens includes antigens which are derived from mutant forms of normal proteins. Examples of this family are MUM-1 (Coulie, et al., *Proc. Natl. Acad. Sci. USA* 92:7976–7980 (1955)); CDK4 (Wölfel, et al., *Science* 269:1281–1284(1955)); Bcatenin (Robbins, et al., *J. Exp. Med.* 183:1185–1192 (1996)); and HLA-A2 (Brandel, et al., *J. Exp. Med.* 183:2501–2508(1996)). A third category, also discussed, supra, includes the differentiation antigens which are expressed by both melanoma and melanocytes. Exemplary are tyrosinase, gp100, gp75, and Melan A/Mart-1. See U.S. Pat. No. 5,620,886 incorporated by reference, with respect to Melan-A. See Wölfel, et al., *Eur. J. Immunol.* 24:759 (1994) and Brichard, et al., *Eur. J. Immunol.* 26:224 (1996) for tyrosinase; Kang, et al., *J. Immunol.* 155:1343 (1995); Cox, et al., *Science* 264:716 (1994); Kawakami, et al., *J. Immunol.* 154:3961 (1995) for gp 100; Wang, et al., *J. Exp. Med.* 183:1131 (1996)for gp75.

There are several approaches that are available for identifying HLA restricted peptides. For example, Boon, et al., *J. Exp. Med.* 183:725–729 (1996), describes how to identify peptides targets of CD8+ T cells with reactivity for autologous melanoma cells. The methodology requires transfer of antigen expression to non-expressing cells, via either cosmids or cDNA vectors. See Van der Bruggen, et al., *Science* 254:1643–1650 (1991); and Kawakami, et al., *Proc. Natl. Acad. Sci. USA* 91:6458–6492 (1994), respectively, both of which are incorporated by reference. In each case, the transfecting molecule must encode the relevant antigen. Where necessary, an HLA-Class I restriction element can also be used. See DePlaen, et al., *Methods* 12:125–142 (1997).

When coding sequences for T cell recognized tumor antigens have been defined, HLA bindings motif analysis, such as that provided by Falk, et al., *Nature* 357:290–296 (1991) can be very useful in identifying relevant peptides.

Hunt et al., Science 255: 1261–1263 (1992) describe a method for identifying peptides by eluting these from HLA molecules, fractionating them via HPLC, and then employing structural identification techniques. Examples of the use of this methodology can be seen in Cox, et al., *Science* 264:716–719 (1994); Skipper, et al., *J. Exp. Med.* 183:527–534 (1996); and Castelli, et al., *J. Exp. Med.* 181:363–368 (1995). There are technical challenges involved in this approach, and it has not been applied widely.

An approach to identifying peptide targets of known tumor antigens which use viral vectors is known. The technique includes inducing a de vovo specific response by naive T cells (Chaux, et al., *J. Immunol.* 163:2928–2936 (1999); Butterfield, et al., *J. Immunol.* 161:5607–5613 (1998)); and in stimulating and expanding in vivo sensitized T cells. See, e.g. Toso, et al *Canc. Res.* 56:16–20 (1996); Yee, et al., *J. Immunol.* 157:4079–4086 (1996); Kim, et al., J. Immunother. 20:276–286 (1997); Ferrari, et al., *Blood* 90:2406–2416 (1997). The T cells are then used to identify naturally processed tumor peptides eliciting a T cell response.

One of the drawbacks of the work described supra is the emphasis on HLA-A alleles, particularly HLA-A2 presentation. Very little is known about MHC/HLA restriction for other MHC/HLA molecules. Of the MHC/HLA molecules which are not an HLA-A subtype, the HLA-B27 molecule has been studied most extensively. See, e.g., Parker, et al, *J. Immunol.* 152:163 (1994), incorporated by reference. Its frequency would suggest that, in a given molecule that is processed to MHC/HLA ligands and/or epitopes, HLA-B27 binders might be expected. As will be shown, however, this was not the case with the invention described herein.

In contrast to HLA-A2 and HLA-B27, information on HLA-C molecules and their binding peptides is scant. Binding motifs are not well characterized, and few peptides have been tested. The frequency of HLA-C occurrence is much lower than the occurrence of HLA-A and B molecules, and the HLA-C molecules are far from the first choice for investigation in a population pool. One of the unexpected findings of the work described herein was the identification of two HLA-C epitopes, as there was little to suggest these in the literature and, as will be elaborated on herein, from the experimental design.

The molecule referred to as "NY-ESO-1", as described in, e.g., U.S. Pat. No. 5,804,381, incorporated by reference, is recognized as one of the most immunogenic of tumor antigens. Nearly half of patients with advanced cancer express the antigen (Stockert, et al., *J. Ex . Med.* 187:1349–1354 (1998)), and the expression is accompanied by both a strong CD4+ and a strong CD8+ T cell response. See Jäger, et al., *J. Exp. Med.* 191:625–630 (2000); Jäger et al., *J. Exp. Med.* 167:265–270 (1998); Jäger, et al., *Proc. Natl. Acad. Sci. USA* 97:4760–4765 (2000); Chen, et al., *J. Immunol.* [press]. Peptides derived from the molecule which are HLA-A2 epitopes are known (Jäger, et al., *J. Exp. Med.* 187:265–270 (1998)); and Wang et al., *J. Immunol.* 161:3598–3600 (1998), describes HLA-A31 binding epitopes.

It has now been found that NY-ESO-1 also presents epitopes which bind to HLA-C molecules, such as HLA-Cw3 and HLA-Cw6. See, e.g., p. 7, line 13 after ". . . HLA-Cw3 and HLA-Cw6." NY-ESO-1 has a homologous sequence to another tumor rejection antigen called LAGE-1 (Lethe et al. U.S. Pat. No. 5,811,519). It follows from what is known about the MAGE-A1/HLA-A1 and MAGE-A3/HLA-A1 peptides that the equivalent regions of LAGE-1 encoding the relevant nonapeptides would also present epitopes which bind with HLA-C molecules, such as HLA-Cw3 and HLA-Cw6. These peptides, and the ramifications of their discovery, are a part of the invention. Also a part of the invention is the methodology by which they were identified. All facets of the invention are elaborated in the disclosure which follows.

DETAILED DESCRIPTION OF PREFERRED EMBODIMENTS

EXAMPLE 1

These experiments describe how cell samples were prepared for use in additional experiments.

Peripheral blood lymphocytes ("PBLs" hereafter) were collected from cancer patients, using standard methodologies. They were then treated to remove CD8+ T lymphocytes, using magnetic beads coated with CD8 specific antibodies, and art recognized techniques. Once the separation had taken place, the CD8+ cells were seeded into round bottomed 96 well plates at $5 \times 10^5$ cells per well, to which RPMI medium 1640, supplemented with 10% human AB serum, L-glutamine (2 mM), penicillin (100 U/ml), streptomycin (100 µg/ml) and 1% non essential amino acids.

The PBLs depleted of CD8+ cells were used as antigen presenting cells ("APCs" hereafter). As will be elaborated in more detail, infra, these cells were either pulsed with 10 µM of peptide, or infected with adenoviral constructs, at 1000IU/cell, overnight, at 37° C. in 300 µl of serum free medium.

EXAMPLE 2

The expression of NY-ESO-1 protein in CD8 depleted PBLs was determined. CD8 depleted PBLs were secured as described supra. These were then transfected with either adenovirus vectors containing cDNA encoding the NY-ESO-1 protein, or an "empty" adenoviral vector. PBLs were secured from both a healthy donor, and a cancer patient.

In order to make the vectors, the protocol described in Chen, et al., *Proc. Natl. Acad. Sci. USA* 94:1914–1918 (1997), and U.S. Pat. No. 5,804,381, both incorporated by reference, was used. In brief, the vector pBK-CMV NY-ESO-1, which is described in both of these references, was digested with EcoRI and XbaI, yielding an 0.8 kb fragment containing cDNA for NY-ESO-1. This fragment was isolated, and cloned into the EcoRI and XbaI sites of shuttle vector pSV2-ICEU-1 pAd, which is commercially available. The resulting shuttle plasmid, referred to as pSV2-ICEU-1 NY-ESO-1 was then digested with ICEU, yielding an expression cassette that contained the CMV promoter/enhancer, NY-ESO-1 cDNA, and a BGH poly A sequence. This fragment was then isolated and cloned into the unique site ICEU-1 site of "pAd Quick" plasmid. This plasmid was then digested with SmaBI, and the digest was used to transfect 293 cells, resulting in a recombinant adenovirus vector that encoded NY-ESO-1.

PBLs were infected with 1000 IU/cell of the adenoviral constructs, and then incubated overnight at 37° C. Cells were permeabilized, and stained with 1 µg/ml of monoclonal antibody specific for NY-ESO-1, which is described in Stockert, et al., *J. Exp. Med.* 187:1349–1354 (1998), incorporated by reference, and PCT application WO99/53938, both of which are incorporated by reference.

Up to 85% of the infected PBLs expressed the recombinant NY-ESO-1 cells, indicating that the approach could be used in additional experiments.

EXAMPLE 3

These experiments determined whether stimulation with NY-ESO-1 recombinant adenovirus infected APCs was comparable to stimulation with APCs that had been pulsed with peptide. These experiments also provide a method for analyzing the occurrence and frequency of NY-ESO-1 reactive T cells in cancer patients. More importantly, by suing recombinant virus vectors to transduce expression of NY-ESO-1 in the APC's rather than exogenous peptides such as SEQ ID NO: 1, this analysis can be done in the context of naturally processed and presented peptide epitopes.

In these experiments, cell samples were taken from two patients who had been identified, previously, as having spontaneous T cell responses to HLA-A2 restricted peptide SLLMWITQC (SEQ ID NO: 1), described in Jäger, et al.,*J. Exp. Med.* 167:265–270 (1998), and Jäger, et al., *Proc. Natl. Acad. Sci. USA* 97:4760–4765 (2000), both of which are incorporated by reference. The PBLs taken from the two patients were treated, as described supra, to separate CD8+ cells therefrom. The CD8 depleted PBLs were then either pulsed with 10 µM samples of SEQ ID NO: 1, transfected with adenovirus encoding NY-ESO-1, as described supra, or with adenovirus encoding green fluorescent protein. Autologous CD8+ cells were then stimulated with the PBLs, for eight days. Stimulation was carried out by adding 1×10$^6$ APCs per well of CD8+ cells, as described, supra (i.e., adding these to wells containing 5×10$^5$ CD8+ cells/well). After 8 hours of stimulation, IL-2 was added (10 U/ml), as was IL-7 (20 ng/ml). This procedure was repeated, for three days, until cells were harvested for testing.

Cells were tested in a tetramer assay, by staining the CD8+ T cells in 50 µl PBS containing 1% FCS, with phycoerythrin ("PE") labeled tetramers. Tetramer synthesis followed Altman, et al., *Science* 274:94–96 (1996), incorporated by reference. Tetramers were assembled using SEQ ID NO: 1 as the peptide. Cells were stained for 15 minutes at 37° C., after which a commercially available monoclonal antibody specific for CD8, i.e., "Tricolor—CD8mAb" was added, on ice, for 15 minutes. Cells were washed, and analyzed by flow cytometry.

After 8 days of stimulation, the frequency of tetramer-positive populations were equivalent, i.e., the responses using peptides and adenovirus transfected cells were the same. The response was specific for NY-ESO-1, because when adenovirus encoding green fluorescenceprotein was used, the tetramer staining was negative.

EXAMPLE 4

These experiments were designed to study CD8+ T cells obtained from one subject more fully. Cytospot assays, as described by Jung, et al., *J. Immunol. Meth.* 159:197–207 (1993), incorporated by reference and adopted as described herein, were used. CD8+ T cells, presensitized as described, supra, were mixed with autologous, EBV-B target cells, at a 1:2 ratio, in 300 µl of serum free medium for 30 minutes. Brefeldin A was added to samples, at 10 µg/ml, for an additional 5 hours. The autologous EBV-B cells, referred to supra, were either pulsed with the peptide of SEQ ID NO: 1, or had been transfected with vaccinia vector constructs. The vaccinia virus construct used contained full length NY-ESO-1 cDNA, under the control of vaccinia virus 40K promoter, as taught by Gritz, et al., *J. Virol.* 64:5948–5957 (1990), incorporated by reference, and *E. coli* lacZ gene under control of fowlpox virus C1 promoter, as described by Jenkins, et al., *AIDS Res. Hum. Retroviruses* 7:991–998 (1991), incorporated by reference. Foreign sequences were inserted into the thymidine kinase gene of the construct, located in the Hind III region of the genome of vaccinia virus Wyeth strain, following Mazzara, et al., *Meth. Enzymol.* 217:557–581 (1993), incorporated by reference.

Cells were fixed, permeabilized, and stained with the tricolor, CD8 specific mAb described supra, an FITC labeled IFN-γ mAb, and a PE-labeled, TNF-α specific mAb, for 15 minutes at room temperature. Results were analyzed via flow cytometry, via gating on CD8+ lymphocytes.

The results showed that the effector cells that had been stimulated with the adenovirus constructs produced high amounts of both IFN-γ and TNF-α in response to autologous EBV-B cells transfected with the vaccinia virus constructs that encoded NY-ESO-1; however, they did not respond to wild type vaccinia transfectants. No cross reaction between the adenoviral vector used for sensitization, and the vaccinia virus used for read out, was observed. The sensitized effectors had typical characteristics of activated memory T cells, including high expression of CD45RO and low expression of CD62L, and they were maintainable for over a month in culture, without restimulation.

Any CD8+ T cells that were positive to the tetramer described supra were sorted, via flow cytometry using the methods described supra. Two populations were found, i.e., one subpopulation positive to the tetramer, and a second population negative to it.

EXAMPLE 5

These experiments elaborate further analyses of the two subpopulations described supra. Following the sorting, the cells were stimulated with allogeneic feeder PBLs in the presence of 0:1 µg/ml PHA, IL-2 (10U/ml), and IL-7 (20 ng/ml). Each subpopulation was then subjected to ELISPOT analysis in order to determine its specificity. Specifically, flat bottomed, 96 well nitrocellulose plates were coated with IFN-γ (2 µg/ml) and then incubated overnight at 4° C. The plates were then washed with PBS, and blocked with 10% human AB serum for 1 hour, at 37° C. Presensitized CD8+ T cells as described supra were added, in quantities ranging from 1×10$^3$ to 5×10$^4$ cells/well, together with 5×10$^4$ target cells. Target cells were PBLs, pulsed with the peptide of SEQ ID NO: 1, PBLs transfected with vaccinia virus expressing NY-ESO-1, or with EBV-B cells, as described, supra. The cells were incubated for 20 hours in RPMI medium 1640, lacking IL-2 and human serum. Plates were then washed thoroughly with PBS to remove cells, and IFN-γ mAbs (0.2 µg/ml), were added to the wells. After incubation for 2 hours at 37° C., plates were washed and developed with streptavidin alkaline phosphatase (1 µg/ml) for 1 hour at room temperature. Washing followed, and then substrate (5-bromo-4-chloro-3-indolyl phosphate/nitroblue tetrazolium) was added and incubated for 5 minutes. After final washes, plate membranes displayed dark violet spots which were counted under the microscope.

Additional experiments using the tetramer positive subpopulation described supra indicated that CD8$^+$T cells, presensitized with NY-ESO-1 recombinant adenovirus could recall effector cells specifically recognizing HLA-A2 tumor cells expressing NY-ESO-1 as targets. This was ascertained by carrying out the ELISPOT assay described supra, using different melanoma cell lines which express NY-ESO-1. One cell line was chosen which did not express NY-ESO-1. The cell lines chosen all expressed HLA-A2 with the exception of one cell line; however, this was a cell line which did express NY-ESO-1. In summary, of the five melanoma cell lines tested, three expressed both NY-ESO-1 and HLA-A2 molecules, one expressed HLA-A2 but not NY-ESO-1, and one expressed NY-ESO-1 but not HLA-A2.

The results indicated that, for the tetramer positive CD8+ T cells, both NY-ESO-1 and HLA-A2 expression were necessary for recognition.

EXAMPLE 6

As noted, supra, sorting led to a subpopulation of CD8+ T cells which were tetramer negative; however; surprisingly this subpopulation, when tested, did react with autologous EBV-B cells infected with vaccinia virus expressing recombinant NY-ESO-1. This indicated that the NY-ESO-1 protein was being processed to an epitope presented by an MHC molecule other than HLA-A2. As noted in the "Background" section, supra, the HLA-B27 molecule is expressed with some frequency, and a binding motif is known, as per Parker, et al, *J. Immunol.* 152:163 (1994), incorporated by reference. This is a nona- or decamer, having arginine at position 2, and a hydrophobic residue at the C-terminus. Since the patient from whom the T-cells were derived expressed HLA-B27, it was reasonable to assume that the peptide molecule might be presented by this HLA-molecule.

Scansion of the NY-ESO-1 amino acid sequence, using the motif from Parker, yielded eleven peptide sequences which would be expected to bind to HLA-B27 molecules, and act as T cell epitopes. Each of the peptides were synthesized, and tested in the ELISPOT assay described supra. None were positive. The peptides in question were found all along the sequence of NY-ESO-1, i.e., at amino acid positions 42–50, 51–60, 76–85, 80–88, 85–94, 105–113, 124–133, 135–143, 157–165, 159–167, and 163–171. See, e.g. WO99/53938, incorporated by reference, providing the amino acid sequence. As indicated, none gave positive results.

The tetramer negative subpopulation was then tested with a panel of EBV-B cells, taken from healthy donors, and transduced with recombinant virus to express NY-ESO-1 but had varying HLA specificities, i.e.:

| LINE NAME | HLA TYPES |
|---|---|
| 9-EBV | A*0101; A*0301; B*15; B*4406; Cw*0303; Cw*0704 |
| 10-EBV | A*3001; A*3301; B*4501; B*5301; Cw*0602 |
| 19-EBV | A*0201; A*2402; B*2705; B*37.01; Cw*0202; Cw*0602 |
| 20-EBV | A*0301; A*2301; B*0702; B*4403; Cw*0401; Cw*0702 |
| 21-EBV | A*2402; A*3101; B*15; B*2705; Cw*0202; Cw*0303 |
| 26-EBV | A*0201; A*0801; B*5701; Cw*0602; Cw*0701 |
| 32-EBV | A*0101; A*0201; B*0801; B*15; Cw*0303; Cw*0701 |

Samples of each of these EBV cells were transfected with either vaccinia virus encoding NY-ESO-1, or wild type vaccinia virus. The samples were tested in the same way as is described supra. Those cell lines which were HLA-Cw3 positive were capable of presenting NY-ESO-1 to the tetramer negative cell subpopulation. Studies were then carried out to identify which peptide was involved. To do this, long, overlapping peptides were synthesized, using art recognized techniques, to span the entire sequence of NY-ESO-1. These peptides were pulsed on to autologous EBV-B cells, and assayed using ELISPOT, as described supra. Peptides corresponding to amino acids 85–102 and 91–108 were recognized by the CD8+ T cells. A motif for HLA-Cw3 binding is described by Falk et al., *Proc. Natl. Acad. Sci. USA* 90:12005–12009 (1993). Using this motif, a peptide consisting of amino acids 92–100 of NY-ESO-1 was synthesized, and tested. To carry out these tests, cell line 721.221, which is HLA-Class I negative, was transfected with cDNA encoding HLA-Cw3, and then pulsed with peptide. In comparable tests, following transfection with HLA-Cw4, results were negative. Both subtype HLA-Cw*0303 and HLA-Cw*0304 presented the peptide well. Indeed, it was recognized at concentrations less than 1 nM. The sequence of the peptide is:

LAMPFATPM
(SEQ ID NO: 2).

EXAMPLE 7

Given the disclosure supra, these experiments were designed to study spontaneous T cell responses to NY-ESO-1 in individuals who are not HLA-A2 positive.

A patient was selected who was seropositive to NY-ESO-1. PBLs were taken from the patient, and following separation of CD8+ T cells as described supra, effector cells were stimulated, in vitro, by CD8 depleted PBLs that had been infected by the adenovirus construct encoding NY-ESO-1. Following 9 days of culture using the methods set forth supra, nearly 40% of sensitized CD8+ T cells were capable of specifically producing IFN-γ in response to NY-ESO-1 expressed by vaccinia infected, histocompatible EBV B cells. As disclosed supra, overlapping peptides spanning NY-ESO-1 were used to determine that peptides consisting of amino acids 73–90 and 79–96 were recognized by pre-sensitized T-cell effectors from the subject. HLA-Cw6 was identified as a restriction element for this response, using the EBV-B cells described supra. Anchor motifs for HLA-Cw6 are described by Falk, et al., supra. A peptide consisting of amino acids 80–88 (ARGPESRLL; SEQ ID NO: 3) was deduced as the relevant nonamer. The peptide was synthesized, tested as described supra, and its recognition by effector cells in an HLA-Cw*0602 restricted fashion was confirmed.

EXAMPLE 8

Previously, Jäger et al., *Proc. Natl. Acad. Sci. USA* 97:4760–4765 (2000), showed that CD8+ T cell reactivity to NY-ESO-1 was found only in patients with antibodies against the protein. Studies were carried out to determine if this was also the case when the adenovirus/vaccinia cross sensitization procedure described herein was used. To test this, three patients with NY-ESO-1 positive tumors were studied. One patient was seropositive, and the others were seronegative. CD8+ T cells from the seropositive patient were stimulated with CD8 depleted PBLs which had been infected with the adenovirus vector encoding NY-ESO-1 described supra. NY-ESO-1 specific responses were observed against histocompatible EBV-B cells expressing NY-ESO-1 via the vaccinia virus vectors. Both the HLA-A2 restricted peptide (SEQ ID NO: 1), and the HLA-Cw3 restricted peptide (SEQ ID NO: 2), were targets of this response. No responses were seen with the seronegative individuals.

The foregoing examples set forth the features of the invention, which include, inter alia, a method for indentifying T cells, such as CD8+ T cells which are specific to a peptide/MHC complex, where the peptide derives from a protein of interest. In this method a sample believed to contain relevant CD8+ cells is contacted to an antigen presenting cell, such as a dendritic cell, which has been infected with a first viral vector that encodes the protein of interest. Following this contact, the CD8+ cells are then contacted with a second population of antigen presenting cells which have been infected with a second viral vector which also encodes the protein of interest, where the second viral vector is different from the first viral vector. One benefit that is believed to be derived from this approach is that any immune response can be more refined in that it is targeted to the antigen rather than any aspect of the viruses. In a preferred embodiment that first viral vector is an adenovirus vector, preferably one that is non replicative, and the second vector is a vaccinia vector. It will be understood, however, that these may be reversed, and that only one of these two choices can be used, in combination with a second virus that differs from one of these two choices.

As indicated, the method requires an antigen presenting cell, such as a dendritic cell, or some other cell type capable of presenting complexes of an MHC or HLA molecule and a peptide on its surface. In practice, the method preferably involves the use of autologous cells, i.e., antigen presenting cells and CD8+ T cells from the same patient, but the methodology can be carried out with allogeneic cells as well. Use of the method, as is seen by the examples, permits the artisan to identify epitopes that are restricted by their presenting MHC/HLA molecule. As shown herein, the method permit identification of peptides which bind to HLA molecules such as HLA-Cw3 and HLA-Cw6 molecules including, but not being limited to the peptides defined by SEQ ID NOS: 2 and 3. These peptides can be used, e.g., to stimulate production of cytolytic T cells specific for complexes of the HLA molecule and the peptide to identify cells presenting the HLA molecule, and so forth. The peptides can be used therapeutically as, e.g., the single peptide component of a formulation designed to enhance an immune response, or as one of a plurality of more than one peptide. Such compositions may include an additional component, such as an adjuvant. An example of such an adjuvant is GM-CSF, as taught by, e.g., Jäger et al., U.S. Pat. No. incorporated by reference.

The NY-ESO-1 gene and the encoded protein show homology to a molecule referred to, alternatively, as "LAGE" and "LL-1." See, e.g., Lethe, et al, U.S. Pat. No. 5,811,519, incorporated by reference in its entirety. LAGE peptides homologous to SEQ ID NOS: 2 and 3, i.e.:

ITMPFSSPM (SEQ ID NO: 4)

ARRPDSRLL (SEQ ID NO: 5)

are also a part of the invention, as epitopes for HLA-Cw3, subtypes HLA-Cw*0303 and HLA-Cw*0304, in particular, and HL-C26, respectively.

It must be borne in mind that there is a recognized difference in the art between MHC ligands and MHC epitopes. With respect to the former, these are peptides which bind to MHC molecules, but do not provoke a T cell response when so bound. With respect to the latter, MHC epitopes are peptides which do bind to MHC molecules, and stimulate T cells when confronted with a T cell specific for the peptide/MHC complex. Falk et al, cited supra, do provide proposed binding motifs for HLA-Cw*3, HLA-Cw*0301, HLA-Cw*0304, HLA-Cw*0601, HLA-Cw*0602. Falk et al do make a distinction between ligands and epitopes, as is evidenced by their paper. It will be seen that no T cell epitopes have been identified for any of these alleles.

Also a part of the invention are so-called "minigenes," i.e., nucleic acid molecules consisting of a nucleotide sequence that encodes the peptides of interest. The peptides are of a length that permits simple construction of all degenerate sequences which code the epitope of interest. These coding sequences can be made a part of an extended "polytopic" sequence, using methods well known in the art, and can be incorporated into coding vectors where the minigene or genes of interest are operably linked to a promoter, for expression in a host cell.

The minigenes can also be used in concert with genes that encode an MHC molecule of interest, such as HLA-Cw3 or HLA-Cw6 codings sequence. The two sequences can constitute part of a single vector, a pair of vectors which are then used in a kit or some other combination that permits the skilled artisan to use them to stimulate a T cell response, and so forth.

Other features of the invention will be clear to the skilled artisan and need not be reiterated here.

While the invention has been described with respect to certain embodiments, it should be appreciated that many modifications and changes may be made by those of ordinary skill in the art without departing from the spirit of the invention. It is intended that such modification, changes and equivalents fall within the scope of the claims presented herein.

We claim:

1. An isolated peptide consisting of an amino acid sequence as set forth in SEQ ID NO: 3.

2. The isolated peptide of claim 1, wherein said peptide binds to an HLA-Cw6 molecule.

3. The isolated peptide of claim 1, wherein said peptide binds to an HLA-Cw6 molecule to form a complex which is recognized by a cytolytic T cell.

4. The isolated peptide of claim 1, wherein said peptide binds to an HLA-Cw6 molecule to form a complex which is recognized by a cytolytic T cell and which provokes said cytolytic T cell.

5. The isolated peptide of claim 1, wherein said peptide binds to an HLA-Cw6 molecule to form a complex, wherein said complex is recognized by a cytolytic T cell and stimulates production of said cytolytic T cell.

* * * * *

SEQUENCE LISTING

<160> NUMBER OF SEQ ID NOS: 5

<210> SEQ ID NO 1
<211> LENGTH: 9
<212> TYPE: PRT
<213> ORGANISM: Homo sapiens

<400> SEQUENCE: 1

Ser Leu Leu Met Trp Ile Thr Gln Cys
                5

<210> SEQ ID NO 2
<211> LENGTH: 9
<212> TYPE: PRT
<213> ORGANISM: Homo sapiens

<400> SEQUENCE: 2

Leu Ala Met Pro Phe Ala Thr Pro Met
                5

<210> SEQ ID NO 3
<211> LENGTH: 9
<212> TYPE: PRT
<213> ORGANISM: Homo sapiens

<400> SEQUENCE: 3

```
Ala Arg Gly Pro Glu Ser Arg Leu Leu
                5

<210> SEQ ID NO 4
<211> LENGTH: 9
<212> TYPE: PRT
<213> ORGANISM: Homo sapiens

<400> SEQUENCE: 4

Ile Thr Met Pro Phe Ser Ser Pro Met
                5

<210> SEQ ID NO 5
<211> LENGTH: 9
<212> TYPE: PRT
<213> ORGANISM: Homo sapiens

<400> SEQUENCE: 5

Ala Arg Arg Pro Asp Ser Arg Leu Leu
                5
```